United States Patent
Effing

(10) Patent No.: US 8,123,730 B2
(45) Date of Patent: *Feb. 28, 2012

(54) MEDICINAL COMPOSITION AND WOUND CONTACT LAYER WITH A COMPOSITION

(75) Inventor: Jochem Effing, Kelkheim-Fischbach (DE)

(73) Assignee: Paul Hartmann AG, Heidenheim (DE)

( * ) Notice: Subject to any disclaimer, the term of this patent is extended or adjusted under 35 U.S.C. 154(b) by 607 days.

This patent is subject to a terminal disclaimer.

(21) Appl. No.: 12/140,550

(22) Filed: Jun. 17, 2008

(65) Prior Publication Data
US 2008/0249485 A1 Oct. 9, 2008

Related U.S. Application Data

(63) Continuation of application No. PCT/EP2006/012101, filed on Dec. 15, 2006.

(30) Foreign Application Priority Data

Dec. 17, 2005 (DE) .......................... 10 2005 060 461

(51) Int. Cl.
*A61F 13/00* (2006.01)

(52) U.S. Cl. ......... 604/304; 514/777; 514/779; 514/781

(58) Field of Classification Search ..................... 604/19, 604/27, 46, 48, 289, 304–308, 332, 336; 514/969, 7.6, 16.5, 20.9, 154, 565, 600, 626, 514/777–781; 260/17.4 CC; 424/141.1, 424/94.1, 409, 618; 602/41, 48, 58; 428/40.1, 428/40.2, 40.5, 40.6
See application file for complete search history.

(56) References Cited

U.S. PATENT DOCUMENTS

| | | | |
|---|---|---|---|
| 4,503,034 A * | 3/1985 | Maupetit et al. | 424/78.05 |
| 5,681,579 A | 10/1997 | Freeman | |
| 6,375,977 B1 | 4/2002 | Auguste et al. | |
| 6,794,555 B2 | 9/2004 | Apert et al. | |
| 2004/0049145 A1 | 3/2004 | Flick | |
| 2005/0084647 A1* | 4/2005 | Menzies et al. | 428/99 |
| 2005/0142154 A1* | 6/2005 | Blatt et al. | 424/401 |
| 2005/0281762 A1 | 12/2005 | Modak et al. | |
| 2006/0147390 A1* | 7/2006 | Schreiber et al. | 424/47 |
| 2008/0249453 A1* | 10/2008 | Effing | 602/48 |
| 2008/0249486 A1* | 10/2008 | Effing | 604/304 |

FOREIGN PATENT DOCUMENTS

DE  10 2004 031955  1/2006

(Continued)

OTHER PUBLICATIONS

International Search Report—PCT/EP2006/012101—mailed on Oct. 28, 2008.

(Continued)

*Primary Examiner* — Patricia Bianco
*Assistant Examiner* — Benedict L Hanrahan
(74) *Attorney, Agent, or Firm* — Brinks Hofer Gilson & Lione

(57) ABSTRACT

The invention relates to a wound dressing, a wound contact layer and a medicinal composition comprising a hydrophilic base in which hydrocolloids are dispersed, wherein the hydrophilic base comprises at least one emulsifier and the use of said composition is for the treatment of wounds.

16 Claims, 1 Drawing Sheet

FOREIGN PATENT DOCUMENTS

Figure 1:
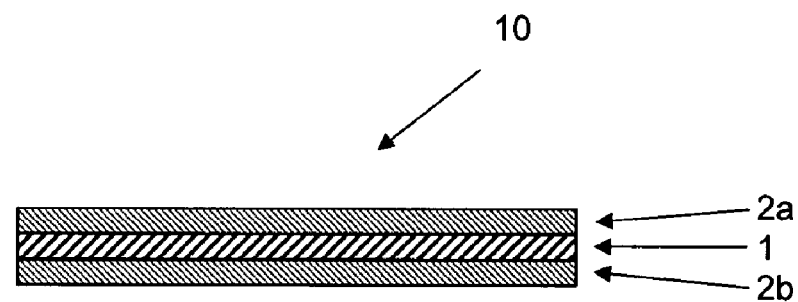

| | | |
|---|---|---|
| DE | 102004031955 A1 | 1/2006 |
| EP | 65399 A1 | 5/1982 |
| EP | 0 065 399 | 11/1982 |
| EP | 0 107 526 | 5/1984 |
| EP | 0107526 A1 | 5/1984 |
| EP | 0 621 031 | 10/1994 |
| EP | 621031 A2 | 10/1994 |
| EP | 1 159 972 | 12/2001 |
| EP | 1 535 605 | 6/2005 |
| EP | 1 535 605 A1 | 6/2005 |
| EP | 1535605 A1 | 6/2005 |
| WO | 96/36315 A | 5/1996 |
| WO | WO 96/36315 | 11/1996 |
| WO | WO 01/60599 | 8/2001 |
| WO | 0170285 | 9/2001 |
| WO | WO 01/70285 | 9/2001 |
| WO | 2005/009403 A1 | 2/2005 |
| WO | 2005009403 | 2/2005 |
| WO | WO 2005/009403 | 2/2005 |

OTHER PUBLICATIONS

International Search Report of PCT/EP2006/012101 Mailed on May 8, 2007 (4 pages).

* cited by examiner

US 8,123,730 B2

MEDICINAL COMPOSITION AND WOUND CONTACT LAYER WITH A COMPOSITION

CROSS-REFERENCE TO RELATED APPLICATIONS

This application is a continuation of International Application No. PCT/EP2006/012101 filed on Dec. 15, 2006, which claims the benefit of DE 10 2005 060 461.7, filed Dec. 17, 2005. The disclosures of the above applications are incorporated herein by reference.

FIELD

The invention concerns a medicinal composition and its use for wound treatment.

BACKGROUND

The statements in this section merely provide background information related to the present disclosure and may not constitute prior art.

A multitude of ointments or other compositions is known and has been used in previous decades as treatment for humans. These ointments are generally semisolid compositions, which are intended for use on healthy skin or some mucosa, such as, for example, on the eyes. These ointments and preparations are usually supposed to have a localized action of percutaneously administering active pharmaceutical ingredients or exerting a softening or protective action on the skin.

Numerous ointments for wound care are furthermore known. EP 621 031, for example, describes a wound ointment which is formulated as a gel and contains at least one gel-forming polysaccharide and hexylene glycol. Carboxymethyl cellulose or sodium alginate in particular should be used as the gel-forming polysaccharide. This composition should have an antimicrobial action and not be toxic with regard to fibroplasts.

Further, EP 107 526 described a paste for protecting the skin, for example, during wound healing or stoma care, which is formulated as a gel containing polyvinyl pyrrolidone, carboxymethyl cellulose, alginate, water, oil, and a fatty acid ester. This gel contains at least 20% water by weight and at least 45% by weight hydrocolloids.

Hydrophilic ointments are furthermore known, which absorb a limited portion of water and can be used for wound care. These ointments contain a mixture of different monoglycerides, diglycerides, and triglycerides, and a nonpolar oil, and are processed, for example, in the products Atrauman® on carrier materials for the production of so-called ointment compresses.

Furthermore a sterile wound dressing is known from EP 65 399, which has a carrier material impregnated with ointment and a water-soluble film of polyvinyl pyrrolidone. The ointment can be a hydrophilic or hydrophobic ointment.

From WO 96/036,315 a sterilizable paste or cream is known which contains an emulsion and a water-insoluble gel-forming material, which can be crosslinked carboxymethyl cellulose. The emulsion for its part should contain oil or wax, water, and an emulsifier, wherein the water content amounts to at least 40% by weight.

From WO 01/070,285 a compress for treating wounds is known which contains a hydrophobic elastomer matrix in which hydrocolloid particles are dispersed. The matrix is supposed to have in addition 55 to 90% by weight nonpolar oil and a surface-active agent with an HLB value higher than 10.

SUMMARY

Considering the state of the art and the disadvantages associated therewith, the present disclosure includes a composition which is suitable for medicinal use, has a positive influence on wound healing, and in addition has a therapeutic effect on the skin surrounding a wound.

A medicinal composition for wound treatment is provided with less than about 10% by weight of water, containing about 60 to about 95% by weight of hydrophilic base, in which about 5 to about 40% by weight of hydrocolloids are dispersed, wherein the hydrophilic base contains about 0.5 to about 50% by weight of at least one emulsifier.

All of the content data is to be understood herein and in the following as percentage by weight based on the total weight of the medicinal composition according to the present disclosure unless otherwise indicated. Further, a medicinal composition in accordance with the present disclosure is to be understood as a hydrophilic base when it is monophasic or multiphasic and is available as an emulsion due to the presence of at least one emulsifier, or is able to form an emulsion. These emulsions can be emulsions containing at least one water and/or gel phase and at least one oil phase.

One advantage of this composition is that this composition can absorb very quickly a large amount of liquids such as wound exudate, for example, due to the content of hydrocolloids dispersed in the hydrophilic base. The hydrophilic base forms an emulsion within a short time when it comes in contact with liquids, whereupon the water in the emulsion can be absorbed in a second step from the dispersed hydrocolloids distributed in the base. This process can also be carried out in parallel. In any case, the hydrocolloids form a second liquid reservoir along with the forming emulsion.

In another form of the medicinal composition, the hydrophilic base should be anhydrous. This hydrophilic base is thus present as a monophasic mixture and is capable of forming an emulsion owing to the presence of at least one emulsifier when water, for example, is added. Here and below, in connection with the invention this means that the hydrophilic base can contain traces of water, whereby the content of water should amount at most to about 1% by weight based on the weight of the hydrophilic base.

In another form, the composition has a hydrophilic base, which is a cream, cream base, or ointment. The hydrophilic base is in particular a hydrophilic cream or cream base, or a hydrophilic ointment. Here and within the context of this application, an ointment should be understood as a monophasic system, whereas a cream is a biphasic or multiphasic system. An accurate differentiation of these formulations also in the classification of further formulations is provided in the German Pharmacopoeia DAB 9 and its commentary, and reference to it is expressly made herein.

It is furthermore especially provided that the composition contains a hydrophilic base, which furthermore contains about 10 to about 30% by weight of nonpolar lipids.

Within the scope of the disclosure, the term "lipids' is used as a generic term for fats, oils, waxes, and the like. The terms "oil phase" and "lipid phase" are also utilized as synonyms. Lipids differ in their polarity, among other things. It has already been proposed to adopt the interfacial tension with reference to water as a measure of the polarity of a lipid or a lipid phase. This means that the polarity of the corresponding lipid phase is greater the lower the interfacial tension between this lipid phase and water. The interfacial tension is considered according to the invention as a possible measure of the polarity of a given oil component. The interfacial tension is therein the force which acts on a line having a length of one meter located in the interface between two phases. The physical unit for this interfacial tension is traditionally calculated according to the force/length ratio, and is usually given in mN/m. It has a positive sign when it tends to reduce the interface. In the opposite case, it has a negative sign. In the sense of the invention, lipids are considered in particular as polar when their interfacial tension with respect to water amounts to less than 20 mN/m, and as nonpolar when their interfacial tension with respect to water amounts to more than 30 mN/m. Lipids with an interfacial tension with respect to water between 20 and 30 mN/m are generally termed midpolar.

Nonpolar lipids are in particular those lipids which are selected from the group of branched and unbranched hydrocarbons and hydrocarbon waxes, in particular vaseline, petrolatum, paraffin oil, mineral oil, and polyisobutene.

Besides nonpolar lipid components, the hydrophilic base can also contain polar and midpolar lipids. Polar or midpolar lipids are, for example, those from the group of fatty acid triglycerides, fatty acid diglycerides, fatty acid monoglycerides, or fatty acid esters of glycerol oligomers, such as, for example, full or partial fatty acid esters of diglycerin or triglycerin. In particular they can be triglyceride, diglyceride and monoglyceride esters of saturated and/or unsaturated, branched and/or unbranched alkane carbonic acids having a chain length of 8 to 24, in particular 12 to 18 C atoms. The fatty acid triglycerides, fatty acid diglycerides, or fatty acid monoglycerides can be advantageously selected, for example, from the group of the synthetic, semisynthetic and natural fats or oils.

A mixture containing a portion of polar and nonpolar lipids and 0.5-30% by weight of at least one emulsifier, whereby the proportion of midpolar and polar lipids in the hydrophilic base with respect to the nonpolar lipids amounts to more than 1:1, in particular more than 2:1, and very preferably between 3:1 and 10:1 based on the total content of lipids, is particularly considered as a hydrophilic base in connection with the present disclosure.

A composition according to the disclosure features in particular a hydrophilic base containing about 20-80% by weight of monoglycerides, diglycerides and/or triglycerides and/or full or partial esters of glycerol oligomers based on the total weight of the composition.

The hydrophilic base contains in particular about 30-70% by weight and more particularly about 40-70% by weight of monoglycerides, diglycerides and/or triglycerides and/or full or partial esters of glycerol oligomers based on the total weight of the composition. Here it is particularly advantageous when the composition contains about 10-50% by weight of monoglycerides, diglycerides and/or triglycerides, and about 10-30% by weight of partial esters of oligomeric glycerin, in particular of diglycerin or triglycerin.

In another form, a composition according to the disclosure has a hydrophilic base containing about 40-80% by weight of monoglycerides, diglycerides, triglycerides and/or partial esters of glycerol oligomers, in particular of diglycerin or triglycerin, about 15-30% by weight of nonpolar fats, and about 0.5-30% by weight of emulsifier based on the total weight of the composition.

Substances featuring surface-active agent activity, so that a multiphasic mixture, namely an emulsion, can be formed when water is added to the hydrophilic base, should be understood as emulsifiers in connection with the invention. In particular, a composition according to the invention should contain at least one emulsifier, by means of which the hydrophilic base is able to form a water-in-oil emulsion (W/O emulsion), gel-in-oil emulsion (G/O emulsion), oil-in-water emulsion (O/W emulsion), oil-in-gel emulsion (O/G emulsion), water-in-oil-in-water emulsion (W/O/W emulsion), gel-in-oil-in-gel emulsion (G/O/G emulsion), gel-in-oil-in-water emulsion (G/O/W emulsion), water-in-oil-in-gel emulsion (W/O/G emulsion) [sic], oil-in-water-in-oil emulsion (O/W/O emulsion), or oil-in-gel-in-oil emulsion (O/G/O emulsion) when water is added. Likewise preferred are emulsifiers that are able to form an O/W or W/O emulsion or an O/G or G/O emulsion and are free of ethylene or propylene glycols or ethylene propylene glycols, that is, they do not contain any substances containing ethylene, propylene, or ethylene propylene glycol units.

A composition according to the disclosure can hereby also feature in particular about 0.5-50% by weight of at least one emulsifier, in particular about 0.5-40% by weight of at least one emulsifier, in particular about 0.5-30% by weight of at least one emulsifier, in particular about 1-20% by weight of at least one emulsifier, and quite preferably about 1-10% by weight of at least one emulsifier.

In another form, a composition according to the disclosure thus contains less than about 10% by weight of water and about 60 to 95% by weight of hydrophilic base, in about 5 to 40% by weight of hydrocolloids which are dispersed, whereby the hydrophilic base contains about 0.5 to 50% by weight of at least one O/W emulsifier. However, it can also be provided that a nonionic W/O emulsifier is used instead of the O/W emulsifier.

When an emulsifier of the O/W type is used, it is advantageous that when the composition is applied, the complete composition can be washed away particularly easily from a wound by means of water, for example.

Furthermore, a composition according to the disclosure can preferably contain at least one nonionic emulsifier with an HLB value of 3 to 18 according to the definitions listed in the Römpp Chemistry Lexicon (J. Falbe, M. Regitz editors), 10th edition, Georg Thieme Publishers Stuttgart, New York (1997), page 1764. Nonionic O/W emulsifiers with an HLB value of 10 to 15 as well as nonionic W/O emulsifiers with an HLB value of 3 to 6 are particularly preferred according to the invention.

The emulsifier or emulsifiers, in particular nonionic O/W emulsifiers, can be advantageously selected from the group of:

Fatty alcohol ethoxylates having the general formula $R-O-(CH_2-CH_2-O)_n-H$ or fatty alcohol propoxylates having the general formula $R-O-(CH_2-CH(CH_3)-O)_n-H$, wherein R represents a branched or unbranched alkyl or alkenyl radical and n represents a number from 10 to 50, Ethoxylated or Propoxylated Lanolin Alcohols, Polyethylene glycol ethers having the general formula $R-O-(CH_2-CH_2-O)_n-R'$ or polypropylene glycol ethers having the general formula $R-O-(CH_2-CH(CH_3)-O)_n-R'$, wherein R and R' represent independently other branched or unbranched alkyl or alkenyl radicals and n represents a number from 10 to 80, Fatty acid ethoxylates having the general formula $R-COO-(CH_2-CH_2-O)_n-H$ or fatty acid propoxylates having the general formula $R-COO-(CH_2-CH(CH_3)-O)_n-H$, wherein R represents a branched or unbranched alkyl or alkenyl radical and n represents a number from 10 to 40, Etherified fatty acid ethoxylates having the general formula $R-COO-(CH_2-CH_2-O)_n-R'$ or etherified fatty acid propoxylates having the general formula $R-COO-$ $(CH_2—CH(CH_3)—O)_n—R'$, wherein R and R' represent independently branched and unbranched alkyl and alkenyl radicals and n represents a number from 10 to 80, Esterified fatty acid ethoxylates having the general formula $R—COO—(CH_2—CH_2—O)_n—C(O)—R'$ or esterified fatty acid propoxylates having the general formula $R—COO—(CH_2—CH(CH_3)—O)_n—C(O)—R'$, wherein R and R' represent independently branched and unbranched alkyl or alkenyl radicals and n represents a number from 10 to 80, Polyethylene glycol glycerin fatty acid esters or polypropylene glycol glycerin fatty acid esters of saturated and/or unsaturated, branched and/or unbranched fatty acids with a degree of ethoxylation or propoxylation of between 3 and 50, Ethoxylated or propoxylated sorbitan esters having a degree of ethoxylation or propoxylation of 3 to 100, Ethoxylated or propoxylated triglycerides having a degree of ethoxylation or propoxylation of between 3 and 150, Polyoxyethylene sorbitol fatty acid esters based on branched or unbranched alkanoic or alkenoic acids and having a degree of ethoxylation of 5 to 100, for example, of the sorbeth type.

Emulsifiers advantageously used within the scope of the disclosure furthermore include nonionic W/O emulsifiers from the group of dicarbonic acid esters or tricarbonic acid esters. Esters of malonic acid, succinic acid, and adipic acid are particularly suitable among these. Particularly preferred among these are also esters of dicarbonic acids, especially esters of succinic acid, which are formed with saturated or unsaturated and/or linear or branched C8-C24 fatty alcohols and/or glycerin as well as their oligomers, in particular diglycerin or triglycerin. Esters of succinic acid with saturated and branched C8-C24 fatty alcohols and/or glycerin as well as their oligomers, in particular diglycerin or triglycerin have proven to be particularly advantageous as nonionic W/O emulsifiers. Very particularly suitable are dicarbonic acid esters of these, which are formed from succinic acid and saturated and branched C8-C24 fatty alcohols and diglycerin. One such emulsifier is called isostearyl diglyceryl succinate according to the INCI nomenclature and can be obtained under the product name "Imwitor®780." These emulsifiers have the further advantage that they are free of polyethylene glycol, which means that they do not contain any units of ethylene glycol.

Especially, ionic O/W emulsifiers can also be utilized as O/W emulsifiers in connection with the invention. Advantageously, emulsifiers selected from the group of esters of monoglycerides and/or diglycerides of saturated or unsaturated fatty acids with hydroxycarbonic acids and/or tricarbonic acids, can be used as O/W emulsifiers, in particular as ionic O/W emulsifiers. Partially neutralized esters of monoglycerides and/or diglycerides of saturated fatty acids with hydroxycarbonic acids and/or tricarbonic acids, especially of lactic acid and/or citric acid are particularly preferred as O/W emulsifiers. Esters of lactic acid and/or citric acid, which are called glyceryl cocoates [or] citrates [or] lactates according to the INCI nomenclature, are very particularly preferred. These emulsifiers can be obtained, for example, under the product name "IMWITOR® 380" or "IMWITOR® 377." These emulsifiers have the further advantage that they are free of polyethylene glycols, which means that they do not contain any ethylene glycol units.

According to the disclosure, the term hydrocolloid should be understood as a material that is a hydrophilic synthetic or natural polymer material, which is soluble or absorbent and/or swells in water and forms a gel. Preferably a composition according to the invention contains, for example, a hydrocolloid from a synthetic or natural polymer material which is selected from the group of alginic acid and its salts as well as its derivatives, chitin or its derivatives, chitosan or its derivatives, pectin, cellulose or its derivatives, such as cellulose ether or cellulose ester, crosslinked or non-crosslinked carboxyalkyl cellulose or hydroxyalkyl cellulose, polyvinyl alcohol, polyvinyl pyrrolidone, agar, guar gum, or gelatin. Cellulose or its derivatives or salts, alginic acid or its derivatives or salts, as well as mixtures thereof can be very preferably used as hydrocolloid.

The hydrocolloid can be available in the form of fibers as well as in the form of particles and/or fibers dispersed in the composition. The hydrocolloid can be available in particular in the form of particles. The proportion of hydrocolloids in the composition amounts to between 5 and 40% by weight based on the total weight of the composition. The proportion of hydrocolloids can preferably amount to between 5 and 30% by weight, further preferably between 10 and 25% by weight, and particularly preferably between 15 and 25% by weight based on the total weight of the composition.

Hydrocolloids that are in particle form, in which the particles have a water content of less than 10% by weight based on the hydrocolloid particles, are particularly preferred as hydrocolloids.

Hydrocolloids which are intermolecularly or intramolecularly interlaced or crosslinked can also be preferably used. These hydrocolloids are not soluble, for example, in water or saline solutions, that is, these hydrocolloids swell when these liquids are added and have an internal cohesion such that the swollen particles are dispersed in the composition.

According to another form of the present disclosure, a composition according to the invention preferably contains at least one hydrocolloid selected from the group of cellulose derivatives or their salts, alginates or their derivatives, chitin or its derivatives or salts. The origin of the hydrocolloids is immaterial here, that is, these hydrocolloids can be of plant or animal origin or can be synthetically produced, for example, by means of microbiological processes. It is also possible to use hydrocolloids that are of plant or animal origin and are modified by means of chemical synthesis.

In connection with the present disclosure, the group of cellulose derivatives includes in particular cellulose ethers and cellulose esters as well as their salts. Particularly used as cellulose ethers are used here are hydroxyalkyl celluloses, in particular hydroxy-C1-6-alkyl cellulose, such as, for example, hydroxymethyl cellulose, hydroxyethyl cellulose, hydroxypropyl cellulose, or hydroxybutyl cellulose, and quite preferably hydroxymethyl cellulose or hydroxyethyl cellulose. Particularly used as cellulose esters are carboxyalkyl celluloses, in particular carboxy-C1-6-alkyl cellulose, such as, for example, carboxymethyl cellulose, carboxyethyl cellulose, carboxypropyl cellulose, or carboxybutyl cellulose or their salts, and quite preferably carboxymethyl cellulose or carboxyethyl cellulose or their salts.

According to another form, the composition contains at least two different hydrocolloids. Here it has been shown to be particularly advantageous to select the at least two hydrocolloids from the group of cellulose derivatives or their salts, in particular cellulose esters or their salts, alginates or their derivates, and chitin or its derivatives or salts.

Furthermore, a wound ointment containing a medicinal composition of the kind described above is also provided by the present disclosure. In particular a wound ointment with less than 10% by weight of water, containing 60 to 95% by weight of hydrophilic base, in which 5 to 40% by weight of hydrocolloids are dispersed, wherein the hydrophilic base contains 0.5 to 50% by weight of at least one emulsifier, is the object of the invention. This wound ointment can be especially used for moderate to heavy exudating wounds, since the wound exudate is especially absorbed by this wound ointment, on the one hand, and the portion of hydrocolloids that form a reservoir for the liquids make available a moist environment for a wound, on the other hand. The hydrocolloids act in the wound ointment simultaneously as a liquid reservoir as well as a moisturizer.

The wound ointment in one form has less than 10% by weight of water and furthermore contains 60 to 95% by weight of hydrophilic base, in which 5 to 40% by weight of hydrocolloids are dispersed, wherein the hydrophilic base contains 20-35% by weight of nonpolar fats and up to 0.5-30% by weight of at least one emulsifier. The wound ointment according to the disclosure having less than 10% by weight of water quite preferably contains up to between 60 and 95% by weight of a hydrophilic base, in which 5 to 40% by weight of hydrocolloids are dispersed, wherein the hydrophilic base contains 50-80% by weight of monoglycerides, diglycerides, triglycerides and/or partial esters of glycerol oligomers, in particular diglycerin or triglycerin, 20-35% by weight of nonpolar fats and 0.5-30% by weight of at least one emulsifier. In particular, the wound ointment is anhydrous.

The use of a composition with less than 10% by weight of water, containing 60 to 95% by weight of a hydrophilic base, in which 5 to 40% by weight of hydrocolloids are dispersed, wherein the hydrophilic base contains 0.5 to 50% by weight of at least one emulsifier, for the production of an agent for treating wounds is likewise an object of the invention. The agent can be in particular a wound ointment, which is further preferred for treating burn wounds or chronic wounds.

According to another form of the present disclosure, a contact layer containing a carrier material and a medicinal composition is also an object of the invention. A wound contact layer containing a carrier material and a composition with less than 10% by weight of water, containing 60 to 95% by weight of a hydrophilic base, in which 5 to 40% by weight of hydrocolloids are dispersed, wherein the hydrophilic base contains between 0.5 and 50% by weight of at least one emulsifier, is in particular also an object of the invention. By means of the carrier material, it is possible to provide the wound contact layer with a form that is easy to apply, which can be applied continuously on the wound. The composition can be brushed on or otherwise applied to at least one side of the carrier material. It is also possible to apply the composition to both sides of the carrier material or to completely impregnate the carrier material with the composition.

A further advantage with respect to the known wound contact layers is that during the application on the wound, which is usually carried out by trained personnel wearing gloves, the wound contact layer according to the invention does not adhere or stick to the gloves. Thus these wound contact layers are particularly safe to handle.

Application of a composition, in particular an ointment, cream, or cream base on a carrier material in an amount of at least 50 g/m2, in particular 100 g/m2, quite preferably 100 to 450 g/m2, and most preferably 100 to 300 g/m2, is particularly advantageous.

The wound contact layer features especially preferably a carrier material and a composition with less than 10% by weight of water, wherein the composition contains between 60 and 95% by weight of hydrophilic base, in which 5 to 40% by weight of hydrocolloids are dispersed, and wherein the hydrophilic base contains 20-35% by weight of nonpolar fats and 0.5-30% by weight of at least one emulsifier. The wound contact layer comprises quite preferably a carrier material and a composition with less than 10% by weight of water, wherein the composition contains 60 to 95% by weight of a hydrophilic base, in which 5 to 40% by weight of hydrocolloids are dispersed, and wherein the hydrophilic base contains 50-80% by weight of monoglycerides, diglycerides, triglycerides and/or partial esters of glycerol oligomers, in particular diglycerin or triglycerin, 20-35% by weight of nonpolar fats, and 0.5-30% by weight of at least one emulsifier. In particular the composition is anhydrous.

Therapeutic components which promote wound healing in particular are made available to the skin surrounding a wound, the so-called peripheral wound skin, due to the presence of fatty acid glycerides in the composition.

The most diverse materials can be used here as carrier material. It has been discovered that polymer films and foils, polymer foams, and nonwovens, as well as textile materials can be especially advantageously used for this purpose. Especially nonwovens as well as textile materials, such as knitted, warp-knitted, or woven fabrics can be especially used as carrier material in the wound contact layer according to the invention. Hydrophobic knitted, warp-knitted, or woven fabrics, which cannot absorb liquids, can also be very advantageously used herein. A wound contact layer according to the invention comprises in particular a polyamide warp-knitted fabric.

If a textile carrier material is used, the material can also be provided in particular with openings, that is, the carrier material can be provided with holes or can have a mesh shape. It is particularly provided that the carrier material is a warp-knitted, woven, or knitted fabric having holes, whose inside width is 0.3 to 3.0 mm, preferably 0.5 to 2.5 mm, and especially preferably 0.5 to 2.0 mm when the material is in unstretched condition. The holes can assume any desired shape, such as, circular, elliptical, quadratic, hexagonal, or octagonal. These warp-knitted fabrics have a weight per unit area of at least 20 g/m2 to at the most 120 g/m2.

A substance that promotes wound healing can likewise be released through the wound contact layer. These include in particular substances having a fungicide, bactericide, or antimicrobial effect. In a special embodiment, the wound contact layer contains a hydrocolloid, which contains in turn at least one fungicide, bactericide, or antimicrobial substance. Chitosan, silver, silver complexes, silver salts, zinc, zinc salts, or zinc complexes are very particularly suitable for this purpose.

However, an agent that promotes wound healing can also be directly applied to the carrier material. In a further embodiment of the wound contact layer, as carrier material a nonwoven or a textile material, such as a knitted, warp-knitted, or woven fabric, which is coated with an antimicrobial acting metal, preferably silver or silver salts, can be used particularly advantageously. When a carrier material such as this is used, the composition can be applied directly to the metal or metal salt on a first side of the carrier material. It is particularly advantageous therein if the composition is anhydrous.

The fact that the carrier material contains a composition on at least its first side is understood according to the disclosure to mean either that the composition is arranged directly on the carrier material provided with the metal, or a continuous or discontinuous metal layer is first applied to the first side, to which then the composition is applied in turn. Application of the composition to both sides may also be desirable, especially when the dressing is to be tamped into the wound. In this case it is advantageous to also apply the metal coating to both sides or to enclose it in the warp-knitted fabric.

The composition, which can be in particular an ointment or cream, here acts as a mediator between the carrier material provided with the metal and the patient's wound. In this way, a direct contact of the wound with the metal and especially also adhesion to it can be securely prevented. This ointment or cream can furthermore produce a therapeutic effect in the region of the peripheral wound skin. If the wound contact layer does come into contact with the wound by means of the composition, the metal, for example, silver, is released from the wound dressing under the influence of the composition, in particular via the wound exudate, and said metal reaches the wound via the composition. It can be particularly provided that the metal used is especially elemental silver. The metal can be arranged as coating on the carrier material or can be impregnated in the carrier material.

The present disclosure further comprises a wound dressing which comprises a cover layer and a wound contact layer. The wound contact layer here contains a composition or a wound ointment containing a hydrophilic base in which hydrocolloids are dispersed, wherein the hydrophilic base contains at least one emulsifier. The disclosure comprises in particular a wound dressing comprising a cover layer and a wound contact layer, wherein the wound contact layer contains a composition with less than 10% by weight of water, which contains 60 to 95% by weight of a hydrophilic base, in which 5 to 40% by weight of hydrocolloids are dispersed, wherein the hydrophilic base contains up to between 0.5 to 50% by weight of at least one emulsifier.

The present disclosure in particular comprises a wound dressing which comprises a cover layer and a wound contact layer, wherein the wound contact layer comprises a carrier material and a composition with less than 10% by weight of water, which contains in addition 60 to 95% by weight of hydrophilic base, in which 5 to 40% by weight of hydrocolloids are dispersed, wherein the hydrophilic base contains up to between 0.5 to 50% by weight of at least one emulsifier.

According to a further development of the disclosure, the present invention also comprises a wound dressing comprising a cover layer, an absorbing layer, and a wound contact layer, wherein the wound contact layer contains a composition with less than 10% by weight of water, which contains 60 to 95% by weight of a hydrophilic base with 0.5 to 50% by weight of at least one emulsifier, in which 5 to 40% by weight of hydrocolloids are dispersed.

A wound dressing can feature in particular a polymer foil or polymer film as the cover layer. Very particularly preferred are polymer films having a high water vapor permeability. Polyurethane, polyether urethane, polyester urethane, polyether polyamide copolymer, polyacrylate, or polymethacrylate films are particularly suitable for this purpose. A polyurethane film, polyester urethane film, or polyether urethane film is particularly preferred as polymer film. Polymer films having a thickness of 15 to 50 µm, in particular 20 to 40 µm, and very particularly preferably between 25 and 30 µm are, however, also very particularly preferred. The water vapor permeability of the polymer film of the wound dressing has preferably at least 750 g/m2/24 hours, in particular at least 1000 g/m2/24 hours, and very particularly preferably at least 2000 g/m2/24 hours (measured according to DIN 13726).

A wound dressing according to the disclosure can furthermore be made available as a so-called island dressing. The wound contact layer here has a smaller application surface than the cover layer, that is, the wound contact layer is surrounded by a cover layer along its periphery. The cover layer can have an adhesive or be made to be adhesive, so that the entire wound dressing can adhere or stick to the skin of a patient. This application of the adhesive can be over the entire surface or discontinuous or only in specific areas. The used adhesive can be a conventional adhesive, in particular an acrylate adhesive, or a pressure-sensitive adhesive based on polyurethanes. It is preferably a gel adhesive, based in particular on polyurethanes, in particular aqueous polyurethanes. It is in one form a hydrogel adhesive based in particular on aqueous acrylates.

According to another form, the wound dressing can have a cover layer which is coated with an adhesive over its entire surface. The water vapor permeability of this carrier material provided with the adhesive here preferably amounts to at least 1000 g/m2/24 hours, in particular at least 1200 g/m2/24 hours, and very preferably to at least 2000 g/m2/24 hours (measured according to DIN EN 13726).

A wound dressing according to the disclosure can be made available in any kind of geometric shape, for example, in triangular, round, oval or square, rectangular or any symmetric or asymmetric shape.

A wound dressing according to the disclosure can furthermore be provided with several layers, which can have the most diverse functions. According to a further development, the wound dressing has at least one further layer. This layer can preferably be a release layer as a protection from contamination, which is applied to the side of the wound contact layer to be placed on the wound when the wound dressing is to be utilized. However, it can also be provided that the wound dressing has at least one further layer between the wound contact layer and the cover layer. This further layer can be an absorbent layer, such as, for example, an absorbent layer of a hydrophilic foam material of polyurethane, for example.

The use of a medicinal composition with less than 10% by weight of water, containing 60 to 95% by weight of a hydrophilic base, in which 5 to 40% by weight of hydrocolloids are dispersed, wherein the hydrophilic base contains up to 0.5 to 50% by weight of at least one emulsifier, for the production of agents, in particular a wound contact layer or a wound dressing for the treatment of wounds, in particular for the treatment of burn wounds or chronic wounds, is provided by the present disclosure.

In another form of the disclosure, it is provided that a wound dressing according to the invention is arranged in a packaging. It is especially provided therein that the packaging is a sterile packaging. In another form, it is provided that a system comprising a wound contact layer of the kind described above and a separate wound dressing are arranged in a package. It is particularly provided therein that the package is a sterile package. In a particular form of this system, each individual component or each group of components is respectively placed in a separate package within the package or sterile package. It can also be provided that each separate package is a separate sterile package.

It should be emphasized at this point that the features of the alternative embodiments of the inventions listed herein are not limited to the individual alternatives. It is rather the case that the combination of embodiments or the combination of individual features of the alternative embodiments can likewise be considered an embodiment according to the invention. The invention should also likewise not be considered limited in any way by the following description of the drawings.

Further areas of applicability will become apparent from the description provided herein. It should be understood that the description and specific examples are intended for purposes of illustration only and are not intended to limit the scope of the present disclosure.

DRAWINGS

Figure 2:
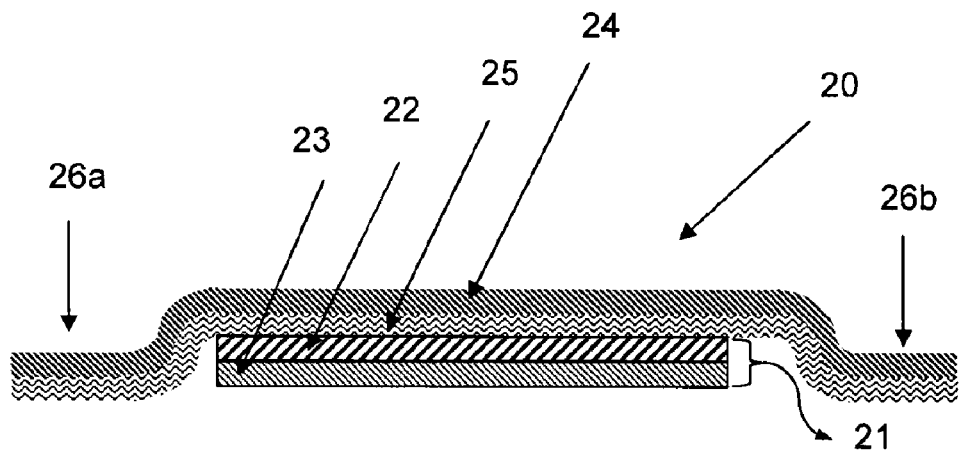

The invention will be described in the following with reference to the drawings and the examples, wherein:

FIG. 1: shows a cross section of the wound contact layer;
FIG. 2: shows a cross section of the wound dressing; and
FIG. 3: shows a cross section of an alternative wound dressing.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

1) Composition 1

| No. | Brand Name | Name - INCI, Function | Content % by Weight |
|---|---|---|---|
| 1 | IMWITOR 780 K (Sasol Company, Witten - Germany) | Isostearyl diglyceryl succinate, nonionic W/O emulsifier HLB 3.7 | 5.0 |
| 2 | IMWITOR 900 K (Sasol Company, Witten - Germany) | Glyceryl stearate, Coemulsifier | 4.0 |
| 3 | SOFTISAN 100 (Sasol Company, Witten - Germany) | Hydrogenated cocoglycerides, polar fat | 4.0 |
| 4 | SOFTISAN 378 (Sasol Company, Witten - Germany) | Caprylic/capric/myristic/ stearic triglycerides, polar fat | 23.0 |
| 5 | SOFTISAN 649 (Sasol Company, Witten - Germany) | Bis-diglyceryl polyacyladipate-2, polar fat | 19.0 |
| 6 | MERKUR Vaseline 115 (Merkur Vaseline GmbH & Co. KG, Hamburg - Germany) | Petrolatum, nonpolar lipid | 25.0 |
| 7 | Blanose 7H3SXF (Herkules Company - Germany) | Cellulose gum, sodium carboxymethyl cellulose, hydrocolloid | 20.0 |

Production of Composition 1:
Phase A (components 1 through 6) is melted and stirred at approximately 75-80° C.
Phase B (component 7) is then dispersed in phase A under energetic stirring. The ointment compound is cooled under energetic stirring, so that a fine crystal structure is produced. The drop point of the composition is 46° C. (determined according to Ph. Eur. 2002, Method 2.2.17).

2) Composition 2

| No. | Brand Name (Manufacturer) | Name - INCI, Function | Content % by Weight |
|---|---|---|---|
| 1 | IMWITOR 377 (Sasol Company, Witten - Germany) | Glyceryl laurate citrate, nonionic O/W emulsifier | 5.0 |
| 2 | IMWITOR 900 K (Sasol Company, Witten - Germany) | Glyceryl stearate, coemulsifier | 4.0 |
| 3 | SOFTISAN 100 (Sasol Company, Witten - Germany) | Hydrogenated cocoglycerides, polar fat | 4.0 |
| 4 | SOFTISAN 378 (Sasol Company, Witten - Germany) | Caprylic/capric/myristic/ stearic triglycerides, polar fat | 23.0 |
| 5 | SOFTISAN 649 (Sasol Company, Witten - Germany) | Bis-diglyceryl polyacyladipate-2, polar fat | 19.0 |
| 6 | MERKUR Vaseline 115 (Merkur Vaseline GmbH & Co. KG, Hamburg - Germany) | Petrolatum, nonpolar lipid | 25.0 |
| 7 | Blanose 7H3SXF (Herkules Company - Germany) | Cellulose gum, sodium carboxymethyl cellulose, hydrocolloid | 20.0 |

Production of Composition 2:
Phase A (components 1 through 6) is melted and stirred at approximately 75-80° C.
Phase B (component 7) is then dispersed in phase A under energetic stirring. The ointment compound is cooled under energetic stirring, so that a fine crystal structure is produced. The drop point of the composition is 48° C. (determined according to Ph. Eur. 2002, Method 2.2.17).

3) Wound Contact Layer 1
The existing wound contact layer has the structure shown in FIG. 1. According to it, the wound contact layer (10) has a carrier material (1) made of hydrophobic 100% polyester warp-knitted fabric (Theodor Preuss GmbH & Co. KG, Ubstach-Weiher—Germany), which is coated on both sides or surfaces with a composition (2a and 2b) of example 1 according to the invention. The composition wets the carrier material completely, wherein the application amount on each side amounts to 140 g/m². The carrier material fabric has a weight per unit area of 63 g/m² (unstretched) and has approximately 40 hexagonal openings per 100 cm (not shown in FIG. 1). The maximum inside width of the openings amounts to 2 mm. The wound contact layer has good cohesion and can be applied particularly well on a wound to be treated.

4) Wound Contact Layer 2:
This wound contact layer also has a structure like the one shown in FIG. 1. This contact layer (10) has the composition of components disclosed in example 1. The carrier material (1) consists of a hydrophobic 100% polyamide warp-knitted fabric (Theodor Preuss GmbH & Co. KG, Ubstadt-Weiher—Germany) with a weight per unit area of approximately 90 g/m² (unstretched) and has approximately 46 hexagonal openings per 100 cm (not shown in FIG. 1). The maximum inside width of the openings amounts to 0.8-1.0 mm. The coating weight of the composition amounts to 240 g/m².

The textile carrier material is coated with the hydrophilic composition by guiding the carrier material via a guide roller through a warm reservoir bath (40° C.) of hydrophilic composition 1. After passing through the bath, the excess amount of transferred composition is stripped off by means of a squeegee. The coated material is brought to room temperature, assembled, packaged, and sterilized.

5) Wound Contact Layer 3
This wound contact layer also has a structure like the one shown in FIG. 1. In this wound contact layer (10), the composition has the components disclosed in example 2. The carrier material (1) consists of a hydrophobic 100% polyamide warp-knitted fabric (Theodor Preuss GmbH & Co. KG, Ubstadt-Weiher—Germany) with a weight per unit area of approximately 80 g/m² (unstretched) and has approximately 40 hexagonal openings per 100 cm (not shown in FIG. 1). The maximum inside width of the openings amounts to 1.2-1.5 mm. The coating weight of the composition amounts to approximately 330 g/m².

The textile carrier material is coated with the hydrophilic composition by guiding the carrier material via a guide roller through a warm reservoir bath (60° C.) of hydrophilic composition 2. After passing through the bath, the excess amount of transferred composition is stripped off by means of a squeegee. The coated material is brought to room temperature, assembled, packaged, and sterilized.

Measurement of the water absorption of the wound contact layers according to the invention in comparison with commercially available products in a simulated wound environment:

The background of this test consists in obtaining evidence concerning how a wound contact layer behaves on a wound, for example, a moderately exuding or highly exuding wound.

a) The gelatin solution is produced as follows:

i) Production of a Solution A:

At room temperature, 0.277 g of calcium chloride and 8.298 g of sodium chloride are placed in a graduated one-liter cylinder, and the latter is filled up to 1 liter with deionized water. The solution is stirred until the salts are dissolved.

ii) Production of the Gelatin Solutions

To y g of the above solution A are added x g of gelatin powder (type A of pigskin, 175 Bloom, GELITA gelatin, DGF Stoess AG, 69402 Eberbach) to produce an x % gelatin solution.

For this purpose, the gelatin is rapidly added all at once into the solution A, the solution is energetically agitated, so that all of the particles are wetted with the solution, and the resulting mixture is stirred for 24 hours in a water bath at 60° C. Care should be taken that no water escapes. In this manner 20% (x=20, y=80) and 35% (x=35, y=65) [sic] gelatin solutions are produced.

b) After 24 hours, Petri dishes with a diameter of 9 cm are filled with 30 g of the still-warm gelatin solution, closed with the corresponding cover, and cooled to room temperature. The resulting solid gels are utilized for analysis of the test pieces.

c) In order to analyze the wound contact layer according to the invention, 3×3 cm pieces are analyzed by placing these test pieces with one side entirely in the Petri dishes filled with gelatin solution, closing the Petri dishes with the corresponding cover, and allowing them to stand for 24 hours at room temperature. After 24 hours, the absorbed amount of liquid is determined by weighing the test pieces. Care must be taken that the weight of the test pieces in their entirety is determined. If necessary, residue remaining on the gelatin surface can be carefully removed with the aid of a suitable scrape and can be taken into consideration during weighing. The results are shown in Tables 1 and 2, wherein three measurements were carried out per sample and each test piece was separately placed in a Petri dish.

Included in the analysis were: Sample 1: A wound contact layer of the invention according to example 4 sterilized by means of beta radiation (40 kGy);

Sample 2: A wound contact layer of the invention according to example 5 sterilized by means of beta radiation (40 kGy);

Sample 3: Urgotül®, Urgo Company; and

Sample 4: Physiotulle®, Coloplast Company.

TABLE 1

Testing of 20% Gelatin Solution

| Sample | Input weight of sample/g | Output weight of sample after 24 hours/g | Water absorption after 24 hours/g | Water absorption after 24 hours (with reference to input weight) Individual Values | Average Value |
|---|---|---|---|---|---|
| 1 | 0.320 | 0.698 | 0.378 | 118% | 125% |
|   | 0.310 | 0.709 | 0.399 | 129% |   |
|   | 0.320 | 0.726 | 0.406 | 127% |   |
| 2 | 0.410 | 1.054 | 0.644 | 157% | 158% |
|   | 0.500 | 1.283 | 0.783 | 157% |   |
|   | 0.430 | 1.115 | 0.685 | 159% |   |
| 3 | 0.190 | 0.224 | 0.034 | 18% | 15% |
|   | 0.194 | 0.219 | 0.025 | 13% |   |
|   | 0.200 | 0.226 | 0.252 | 13% |   |
| 4 | 0.243 | 0.330 | 0.087 | 36% | 36% |
|   | 0.231 | 0.320 | 0.088 | 38% |   |
|   | 0.235 | 0.315 | 0.080 | 34% |   |

TABLE 2

Testing of 35% Gelatin Solution

| Sample | Input weight/g | Output weight after 24 hours/g | Water absorption after 24 hours/g | Water absorption after 24 hours (with reference to input weight) Individual Values | Average Value |
|---|---|---|---|---|---|
| 1 | 0.308 | 0.577 | 0.269 | 87% | 91% |
|   | 0.318 | 0.575 | 0.257 | 81% #|   |
|   | 0.313 | 0.615 | 0.302 | 96% |   |
| 2 | 0.496 | 1.069 | 0.573 | 116% | 115% |
|   | 0.441 | 0.950 | 0.509 | 115% |   |
|   | 0.449 | 0.965 | 0.516 | 115% |   |
| 3 | 0.189 | 0.226 | 0.037 | 19% | 18% |
|   | 0.190 | 0.225 | 0.035 | 18% |   |
|   | 0.192 | 0.227 | 0.035 | 18% |   |
| 4 | 0.227 | 0.281 | 0.054 | 24% | 25% |
|   | 0.237 | 0.296 | 0.059 | 25% |   |
|   | 0.238 | 0.297 | 0.059 | 25% |   |

Test piece was not fully on the gelatin surface (not considered).

The results shown in Table 1 represent an approximation of the behavior of the wound contact layer on moderate to heavy exuding wounds. According to it, a wound contact layer according to example 5 (sample 2) absorbs on average 158% times its own weight in liquid in 24 hours. In comparison, the product that can be obtained in the market shows much lower moisture absorption. The values are on average 36% for sample 4 and 15% for sample 3. A similar trend can be demonstrated with the results of Table 2. This analysis represents a simulation on a weak to moderate exuding wound. According to it, a wound contact layer according to example 5 (sample 2) absorbs on average 115% times its own weight in liquid in 24 hours. In comparison, the product that can be obtained in the market has a lower moisture absorption capacity. The values are on average 25% for sample 4 and 19% for sample 3. If the results of both tests are compared with each other, it can also be determined that a wound contact layer according to the invention also shows good targeted moisture absorption, which means that more moisture is absorbed from heavy exuding wounds than form more moderate exuding wounds.

6) Wound Dressing 1 A wound dressing (20) according to the invention [configured] as a so-called island dressing is shown in FIG. 2. The wound dressing consists of a cover layer (24) and a wound contact layer (21). The wound contact layer consists, in turn, of a carrier material (22), which is a hydrophobic nonwoven of polyester fibers coated with a composition (23) according to example 1. The composition fully covers the polyester nonwoven with a coating amount of 180 g/m² (water jet reinforced, weight per unit area 50 g/m²). The wound contact layer is covered with a cover layer (24), which is coated over its entire surface with a polyacrylate pressure-sensitive adhesive (25). The cover layer is a 30 μm thick polyurethane film with a water vapor permeability of 1100 g/m²/24 hours, which extends on all sides over the peripheral boundaries of the wound contact layer, so that the wound contact layer can be attached to the skin of a patient by means of the adhesive borders of the cover layer (26a, 26b). The wound contact layer (22) is fixed at the same time to the cover layer by means of the pressure-sensitive adhesive (25).

Figure 3:
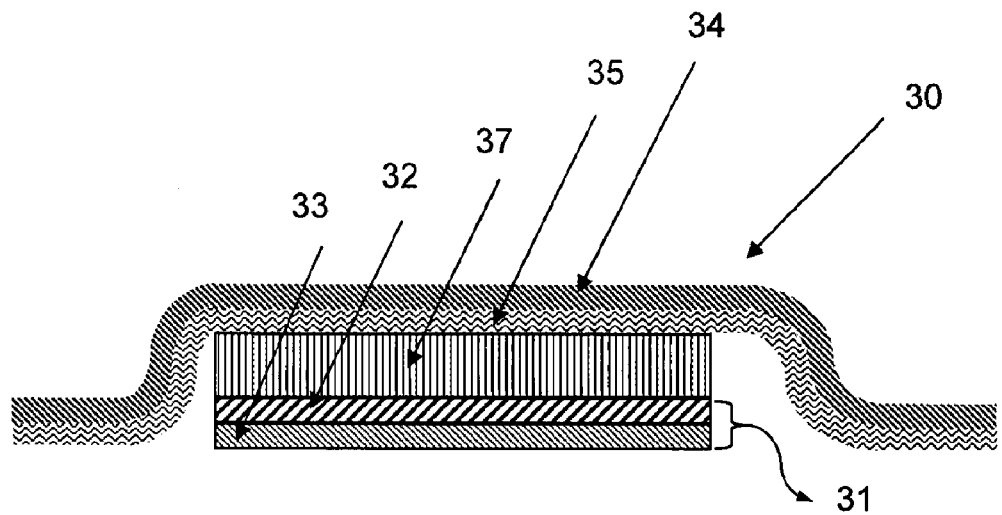

7) Wound Dressing 2. A further wound dressing (30) according to the invention is shown in FIG. 3. It has an additional absorbent layer (37) in comparison with the wound dressing (20) shown in FIG. 2. This additional absorbent layer (37) is made from hydrophilic open-celled polyurethane foam with a weight per unit area of 500 g/m² and a thickness of 5 mm. The absorbent layer is fixed to the cover layer by means of the pressure-sensitive adhesive layer (35) of acrylate dispersion adhesive. The cover layer consists of a polyurethane film with a thickness of 25 μm and a water vapor permeability of 1200 g/m²/24 hours. The wound contact layer (31) consists of a polyamide warp-knitted fabric (32), which is coated with the composition (33) according to example 1 (150 g/m²). The polyamide warp-knitted fabric (Theodor Preuss GmbH & Co. KG, Ubstadt-Weiher—Germany) has 45 hexagonal openings per 100 cm (not shown in FIG. 3). The maximum inside width of the openings is between 0.8 and 1.0 mm. The weight per unit area amounts to 86 g/m². The wound dressing should be used in particular with heavy exuding wounds. The wound dressing treats the peripheral wound skin due to its portion of triglycerides in the composition and does not stick to the wound also during long periods of use.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A medicinal composition for wound treatment containing about 60 to about 95% by weight of hydrophilic base, in which about 5 to about 40% by weight of hydrocolloids are dispersed, wherein said hydrophilic base contains about 0.5 to about 50% by weight of at least one emulsifier, about 20 to about 80% by weight of monoglycerides, diglycerides, and/or triglycerides and/or full or partial esters of glycerol oligomers, about 10 to about 30% by weight of nonpolar lipids, and up to 1% by weight of water, wherein the emulsifier is one of an ionic oil in water emulsifier and a nonionic water in oil emulsifier.

2. The composition of claim 1, characterized in that the hydrophilic base is anhydrous.

3. The composition of claim 1, characterized in that the hydrophilic base is selected from the group consisting of a cream, a cream base, and an ointment.

4. The composition of claim 1, characterized in that the hydrocolloids are available in particle form.

5. The composition of claim 1, characterized in that the hydrocolloids are selected from the group consisting of cellulose or its derivatives or salts as well as alginic acid or its derivatives or salts.

6. A wound dressing comprising a contact layer having a carrier material and the medicinal composition according to claim 1.

7. The wound dressing of claim 6, characterized in that the carrier material is selected from the group consisting of a nonwoven, knitted fabric, warp-knitted fabric, or woven fabric.

8. The wound dressing of claim 6, characterized in that the carrier material is selected from the group consisting of a hydrophobic knitted fabric, a warp-knitted fabric, and a woven fabric.

9. The wound dressing of claim 6, characterized in that the carrier material comprises a polyamide warp-knitted fabric.

10. The wound dressing of claim 6 further comprising a cover layer.

11. The wound dressing of claim 6, characterized in that the wound dressing furthermore comprises an absorbent layer, which is adjacent to the wound contact layer.

12. The composition of claim 1, wherein the nonpolar lipids are selected from the group consisting of Vaseline, petroleum, paraffin oil, and waxes.

13. A wound ointment containing a medicinal composition according to claim 1.

14. A wound contact layer comprising a carrier material and at least one of the medicinal composition according to claim 1 and the wound ointment according to claim 13.

15. The wound contact layer according to claim 14, wherein the carrier material is selected from the group consisting of a nonwoven, a knitted, a warp-knitted, a hydrophobic knitted, a hydrophobic warp-knitted, and a hydrophobic woven fabric.

16. The wound contact layer according to claim 14, wherein the carrier material comprises a polyamide warp-knitted fabric.

* * * * *